(12) United States Patent
Termanini

(10) Patent No.: US 9,155,632 B2
(45) Date of Patent: Oct. 13, 2015

(54) ORTHOPEDIC INSTRUMENT, SYSTEM AND METHOD FOR IMPLANTING AN ACETABULAR CUP

(75) Inventor: Zafer Termanini, Cedar Grove, NJ (US)

(73) Assignee: HIP Innovation Technology, LLC, Plantation, FL (US)

( * ) Notice: Subject to any disclaimer, the term of this patent is extended or adjusted under 35 U.S.C. 154(b) by 111 days.

(21) Appl. No.: 14/236,477

(22) PCT Filed: Jul. 19, 2012

(86) PCT No.: PCT/US2012/047324
§ 371 (c)(1),
(2), (4) Date: Apr. 21, 2014

(87) PCT Pub. No.: WO2013/022586
PCT Pub. Date: Feb. 14, 2013

(65) Prior Publication Data
US 2015/0127113 A1    May 7, 2015

Related U.S. Application Data

(60) Provisional application No. 61/521,030, filed on Aug. 8, 2011.

(51) Int. Cl.
*A61F 2/46* (2006.01)
*A61F 2/34* (2006.01)
*A61B 17/17* (2006.01)
*A61F 2/30* (2006.01)

(52) U.S. Cl.
CPC .......... *A61F 2/4609* (2013.01); *A61B 17/1746* (2013.01); *A61F 2/34* (2013.01); *A61F 2002/305* (2013.01); *A61F 2002/30332* (2013.01); *A61F 2002/3401* (2013.01); *A61F 2002/3483* (2013.01); *A61F 2002/4681* (2013.01)

(58) Field of Classification Search
CPC ....... A61F 2/46; A61F 2/4609; A61F 2/4612; A61F 2/34; A61F 2002/3498; A61F 2/4081; A61F 2002/4096; A61B 17/1664; A61B 17/1666; A61B 17/1746; A61B 17/1684; A61B 2017/1778
See application file for complete search history.

(56) References Cited

U.S. PATENT DOCUMENTS

| 5,540,697 A | 7/1996 | Rehmann et al. |
| 2012/0226283 A1 * | 9/2012 | Meridew et al. ............... 606/81 |

FOREIGN PATENT DOCUMENTS

| DE | 10 2008 022 329 A1 | 5/2009 |
| DE | 102008022329 A1 * | 11/2009 |
| FR | 2 776 182 A1 | 9/1999 |
| WO | WO 2004/069107 A1 | 8/2004 |

OTHER PUBLICATIONS

International Search Report and Written Opinion Sep. 6, 2012.
Supplementary European Search Report dated Jan. 21, 2015.

* cited by examiner

*Primary Examiner* — Thomas J Sweet
*Assistant Examiner* — Daniel Bissing
(74) *Attorney, Agent, or Firm* — Norris McLaughlin & Marcus PA

(57) ABSTRACT

An orthopedic instrument for installing a new reverse hip prosthesis, particularly the acetabular cup thereof, wherein the cup can be affixed to the pelvis with or without screws. The acetabular cup is releasably attached to the instrument and the instrument is used to position the cup in the pelvis. Optional screw guides are provided in the instrument in case the surgeon wishes to use screws to affix the cup to the pelvis.

8 Claims, 5 Drawing Sheets

ORTHOPEDIC INSTRUMENT, SYSTEM AND METHOD FOR IMPLANTING AN ACETABULAR CUP

BACKGROUND OF THE INVENTION

1. Field of the Invention

The present invention has to do with an orthopedic instrument and its use in hip replacement surgery for implanting an acetabular cup in the pelvis of a patient. More specifically, the invention relates to a new orthopedic instrument designed for implanting the reverse hip acetabular cup described in Published PCT Application No. WO 2011-112353-A1, dated Sep. 15, 2011, and entitled "Interlocking Reverse Hip and Revision Prosthesis" and its parent, Published U.S. Patent Application No. 2011-0218637-A1, dated Sep. 8, 2011, the disclosures of which are incorporated herein by reference.

2. The Related Art

The prior art discloses apparatus for implanting various portions of a prosthesis, such as an acetabular cup, into an anatomy. For example, U.S. Pat. No. 7,727,282 discloses an apparatus that rigidly engages a prosthesis member to allow for positioning it relative to the anatomy.

SUMMARY OF THE INVENTION

The orthopedic instrument of the invention was developed to implant a revolutionary new reverse hip prosthesis in a patient. In particular, the instrument is used to position and securely affix the acetabular cup component of the prosthesis in the pelvis of a patient.

Two methods of using the instrument are available to the surgeon. In one method, the acetabular cup is affixed to the pelvis without using screws and in the other method at least one screw is used. Drill guides can be incorporated in the instrument in case the surgeon wishes to use screws.

BRIEF DESCRIPTION OF THE DRAWINGS

The mechanical elements of the invention are illustrated in the drawings summarized as follows.

DESCRIPTION OF THE PREFERRED EMBODIMENTS

Figure 1:
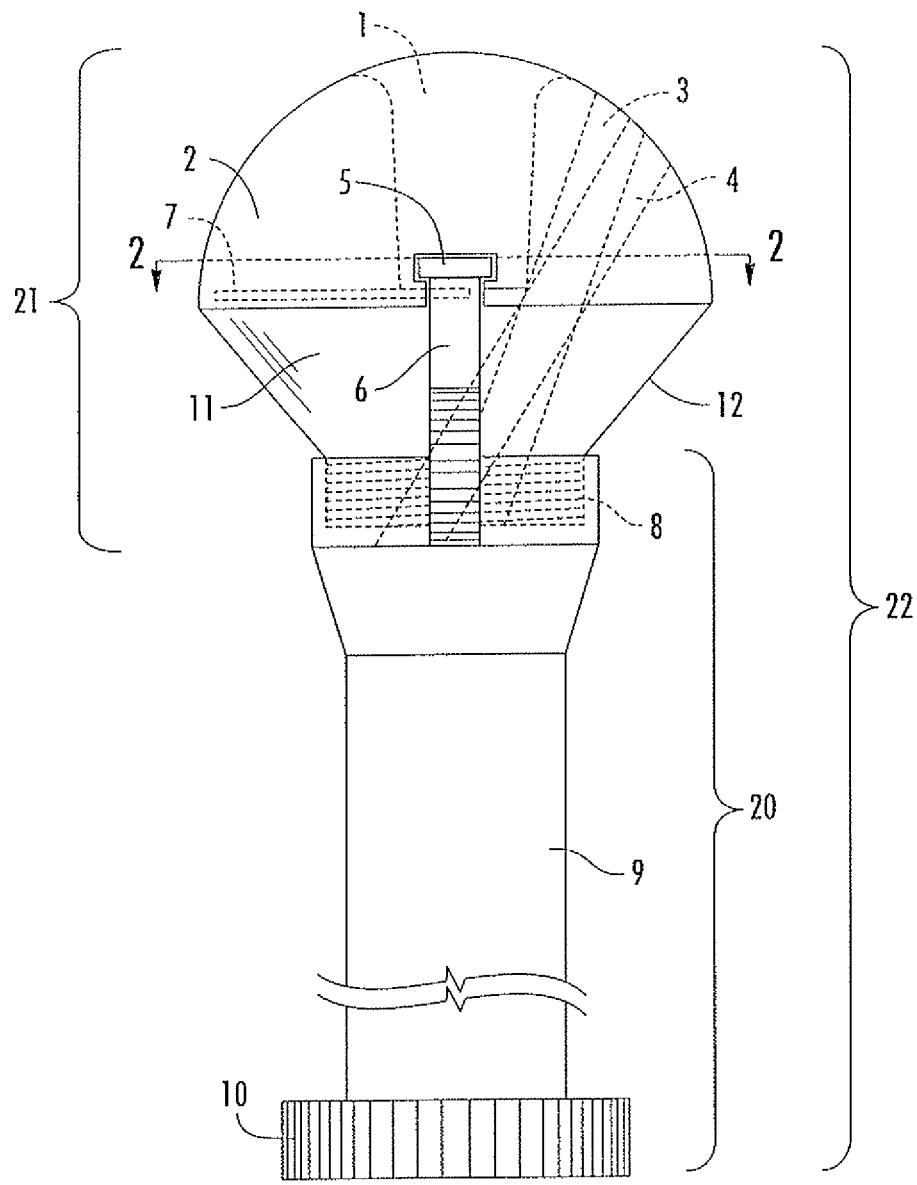
FIG. 1 is a semi-transparent elevational view of the orthopedic instrument.
Figure 2:
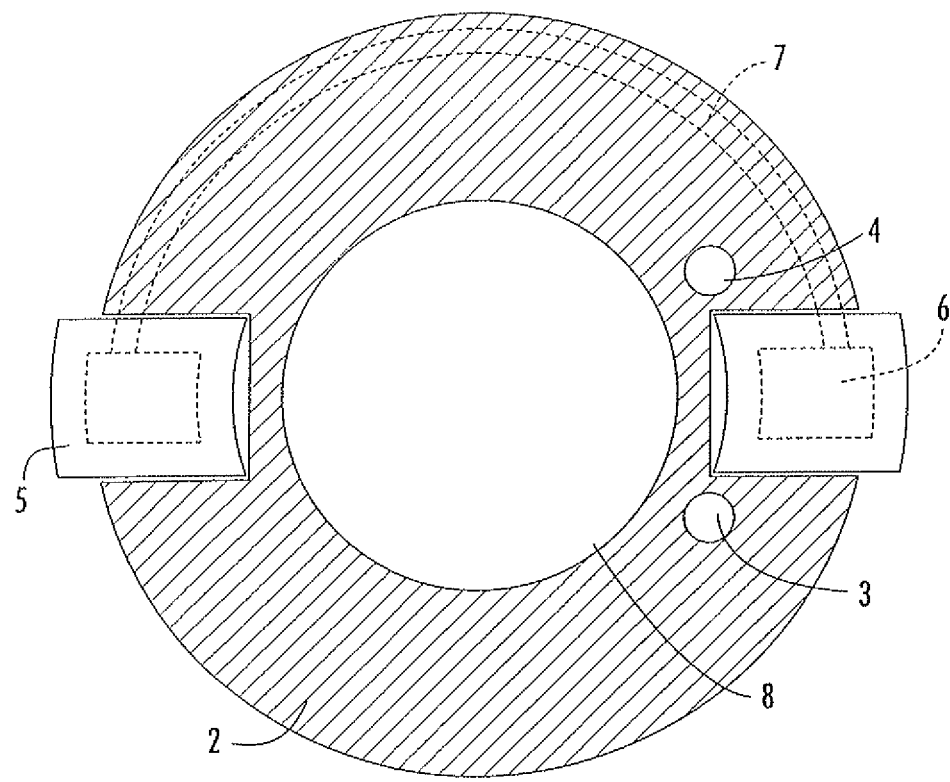
FIG. 2 is a top section view of the acetabular impactor taken along section line 2-2 of FIG. 1.

Referring to the drawings, the main components of the orthopedic instrument 22 are a handle 20 and an acetabular impactor 21. The handle 20 is comprised of a shaft 9, an impactor head 10 at the proximal end of the shaft 9 and a threaded portion at the distal end. The threaded portion of the handle is comprised of an axially disposed, internally threaded annular portion. The acetabular impactor 21 is comprised of threads 8 at the proximal end for removably affixing the acetabular impactor 21 to the handle 20 by screwing the acetabular impactor 21 and handle 20 together. The threads 8 are comprised of an axially disposed externally threaded portion. In a variation of the invention which is not illustrated in the drawings, the threads on the handle can be external and the threads on the acetabular impactor can be internal.

Other elements of the acetabular impactor 21 include recess 1, hemispherical head 2, proximal conical extension 11, retaining tongues 5, release levers 6, hemi-circular retaining ring 7 and recesses 17. The retaining ring 7 acts as a spring to allow the retaining tongues 5 to move laterally to removably engage the acetabular cup 14. Optional elements of the acetabular impactor include conical protective/supportive sheet 12 and channels 3 and 4 as drill guides and for screw insertion.

Figure 3:
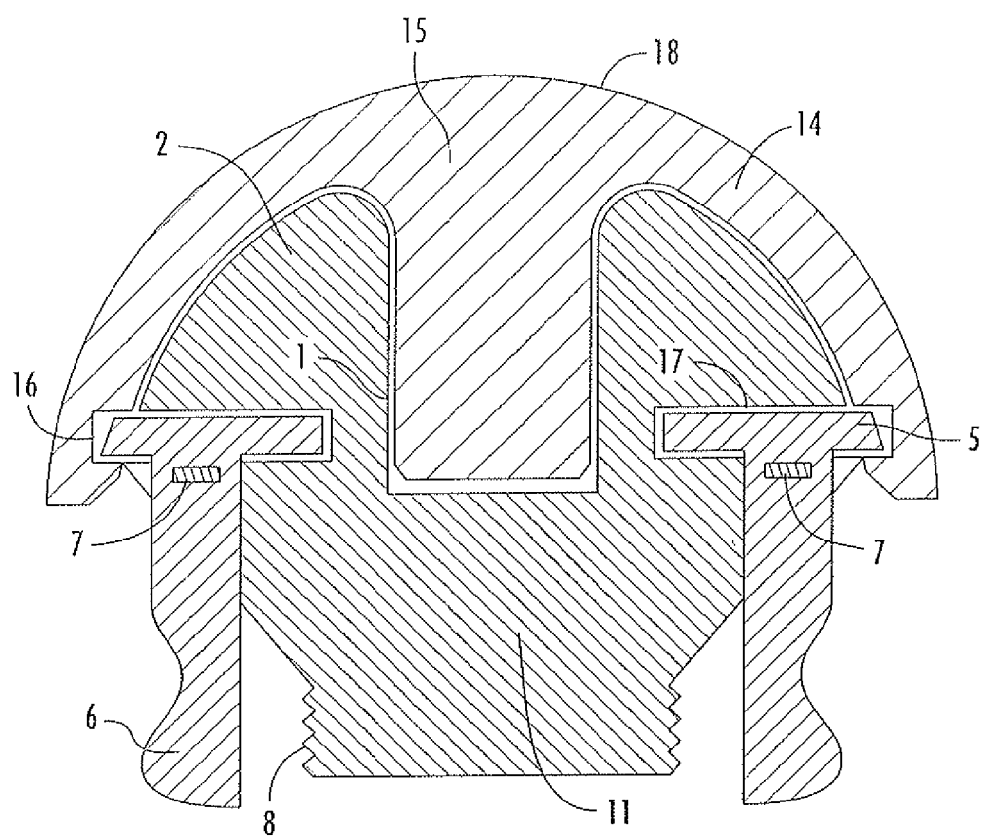
FIG. 3 illustrates a section view of the acetabular impactor with the acetabular cup releasably engaged thereto.
Figure 4:
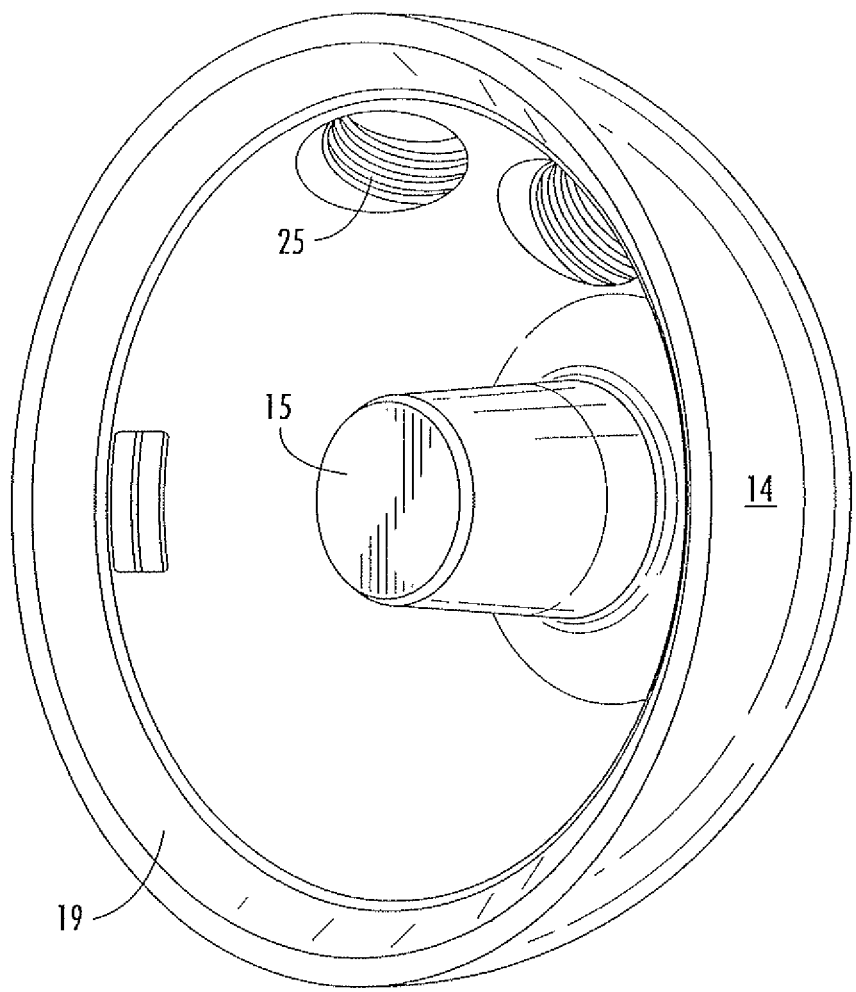
FIG. 4 is a perspective view of the acetabular cup.

The acetabular cup 14 has a stem 15 which is accommodated by recess 1 in acetabular impactor 21. A circumferential groove 16 is located in the concave surface of the acetabular cup in proximity to the circumferential edge of the cup. As illustrated in FIG. 3, the retaining tongues 5 engage the circumferential groove 16 when the acetabular cup is releasably engaged with the orthopedic instrument 22. In a variant of the invention, reference number 16 can designate diametrically opposed recesses for the retaining tongues 5. Surface 18 of the acetabular cup is adapted for secure attachment to the acetabular socket of a pelvis. In a preferred embodiment the surface 18 is convex but other shapes suitable for secure attachment to a pelvic bone can be used as will be apparent to those skilled in the art. Referring to FIG. 4, the screw holes 25 are optionally threaded and preferably are threaded in a portion of the holes having a Morse taper, the taper having a larger diameter on the concave surface 19 of the acetabular cup 14 and a smaller diameter on the opposite side 18, said opposite side preferably having a convex shape.

An orthopedic system is provided according to the invention when the acetabular cup 14 is removably engaged with the orthopedic instrument 22 or when the acetabular cup 14 is removably engaged with the acetabular impactor 21.

There are two methods according to the invention. The first method is employed when the surgeon does not use screws to affix the acetabular cup 14 in the pelvis. The second method is employed when the surgeon uses at least one screw to affix the acetabular cup 14 to the pelvis.

In the first method, the acetabular cup 14 is releasably engaged with the distal end of the orthopedic instrument 22 by snap fitting the cup over the retaining tongues 5 to engage the circumferential groove 16. Then the acetabular cup 14 is positioned in the acetabular socket of the pelvis and the impactor head 10 is impacted, such as with a hammer, to affix the acetabular cup 14 in the acetabular socket. The orthopedic instrument 22 then is released from the acetabular cup by pressing release levers 6 inwardly.

Figure 5:
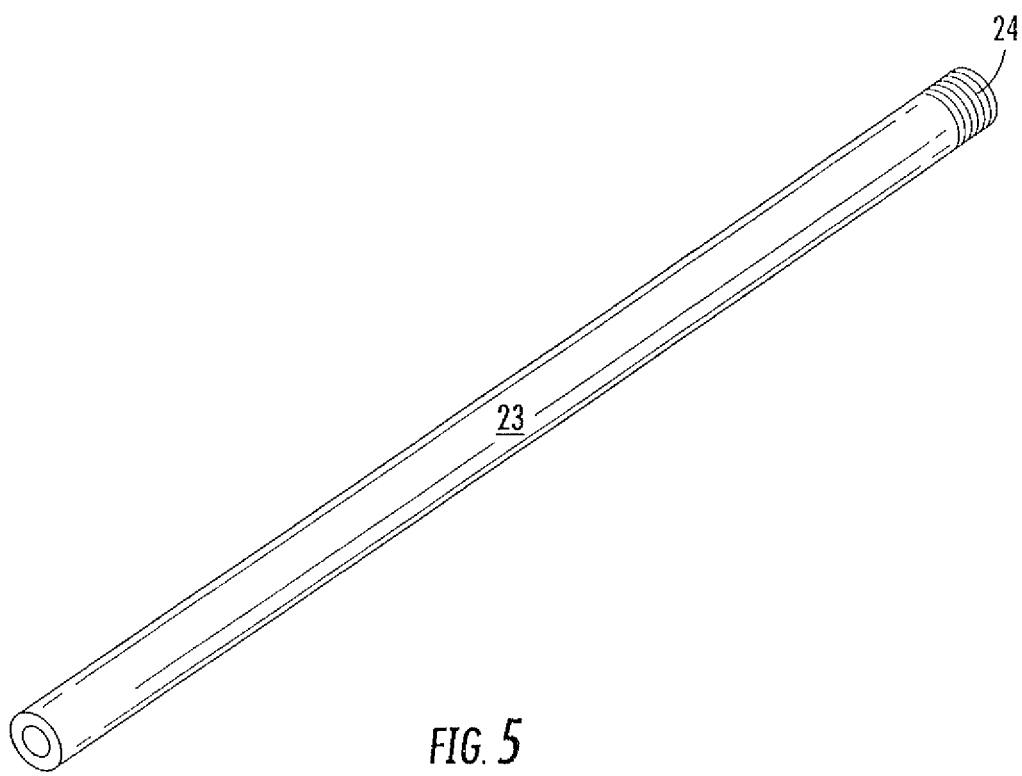
FIG. 5 illustrates in perspective a sleeve used to guide the drill bit when a screw hole is drilled in the pelvic bone.

In the second method, the acetabular cup 14 is releasably engaged with the distal end of the orthopedic instrument 22 in the same manner as described above. Then the acetabular cup 14 is positioned in the acetabular socket of the pelvis and the impactor head 10 is impacted to set the acetabular cup 14 in place. Then the handle 20 is unscrewed from the acetabular impactor 21 and a sleeve 23 of FIG. 5 is inserted into one or both of channels 3 or 4. Sleeve 23 is also optionally provided with threads 24, preferably on a Morse taper, to mate with the threads in screw holes 25. When a sleeve 23 is threaded into a screw hole 25, the sleeve will not spin during drilling and the engagement of the acetabular cup 14 with the acetabular impactor 21 is enhanced. The sleeve 23 is sized with suitable outer and inner diameters to prevent or minimize wobbling of the drill bit during drilling of the pelvic bone. The length of the sleeve 23 is sized to insure that the drill bit penetrates the bone to the appropriate depth without going too deep. After the hole is drilled, the sleeve 23 is removed, the screws are installed and the acetabular impactor 21 is released from the acetabular cup 14 as described above.

What is claimed is:

1. An orthopedic instrument for implanting an acetabular cup having a surface for attachment to an acetabular socket in a pelvic bone and a concave surface having an acetabular cup stem affixed therein and projecting outwardly therefrom, the concave surface further comprising a circumferential groove located in proximity to a circumferential edge of the acetabular cup, the orthopedic instrument comprising
- a handle comprising a shaft having an impactor head at a proximal end and an axially disposed first threaded annular portion at a distal end,
- an acetabular impactor having a hemispherical head at a distal end and an axially disposed second threaded annular portion at a proximal end, the second threaded annular portion being screwed into the first threaded annular portion removably affixing the handle to the acetabular impactor,
- the hemispherical head being configured to couple to the acetabular cup, the hemispherical head comprising an annular recess to receive the acetabular cup stem and retaining tabs configured to releasably engage the circumferential groove.

2. The orthopedic instrument of claim 1, the acetabular cup further comprising at least one screw hole to accommodate a screw for attaching the acetabular cup to the pelvic bone, the acetabular impactor further comprising at least one channel configured as a drill guide.

3. The orthopedic instrument of claim 1 wherein the first threaded annular portion is internally threaded and the second threaded annular portion is externally threaded.

4. The orthopedic instrument of claim 1 wherein the first threded annular portion is externally threaded and the second threaded annular portion is internally threaded.

5. An orthopedic system for implanting an acetabular cup, the system comprising
- an acetabular cup having a surface for attachment to an acetabular socket in a pelvic bone and a concave surface having an acetabular cup stem affixed therein and projecting outwardly therefrom, the concave surface further comprising a circumferential groove, said circumferential groove located in proximity to a circumferential edge of the acetabular cup, and
- an orthopedic instrument comprising
- a handle comprising a shaft having an impactor head at a proximal end and an axially disposed first threaded annular portion at a distal end,
- an acetabular impactor having a hemispherical head at a distal end and an axially disposed second threaded annular portion at a proximal end, the second threaded annular portion being screwed into the first threaded annular portion removably affixing the handle to the acetabular impactor,
- the hemispherical head being releasably coupled to the acetabular cup, the hemispherical head comprising an annular recess to receive the acetabular cup stem and retaining tabs configured to releasably engage the circumferential groove.

6. The orthopedic system of claim 5, the acetabular cup further comprising at least one screw hole to accommodate a screw for attaching the acetabular cup to the pelvic bone, the acetabular impactor further comprising at least one channel configured as a drill guide.

7. A method of using an orthopedic instrument to implant an acetabular cup in a pelvic bone,
- the acetabular cup having a surface for attachment to an acetabular socket in a pelvic bone and a concave surface having an acetabular cup stem affixed therein and projecting outwardly therefrom, the concave surface further comprising a circumferential groove, said circumferential groove located in proximity to a circumferential edge of the acetabular cup, and
- the orthopedic instrument comprising
- a handle comprising a shaft having an impactor head at a proximal end and an axially disposed first threaded annular portion at a distal end,
- an acetabular impactor having a hemispherical head at a distal end and an axially disposed second threaded annular portion at a proximal end, the second threaded annular portion being screwed into the first threaded annular portion removably affixing the handle to the acetabular impactor,
- the hemispherical head being configured to couple to the acetabular cup, the hemispherical head comprising an annular recess to receive the acetabular cup stem and retaining tabs configured to releasably engage the circumferential groove,
- the method comprising releasably engaging the acetabular cup with the orthopedic instrument,
- positioning the acetabular cup in the acetabular socket,
- impacting the impactor head to affix the acetabular cup in the acetabular socket, and
- releasing the orthopedic instrument from the acetabular cup.

8. A method of using an orthopedic instrument to implant an acetabular cup in a pelvic bone,
- the acetabular cup having a surface for attachment to an acetabular socket in a pelvic bone, a concave surface having an acetabular cup stem affixed therein and projecting outwardly therefrom and at least one screw hole to accommodate a screw for attaching the acetabular cup to the pelvic bone, the concave surface further comprising a circumferential groove, said circumferential groove located in proximity to a circumferential edge of the acetabular cup, and
- the orthopedic instrument comprising
- a handle comprising a shaft having an impactor head at a proximal end and an axially disposed first threaded annular portion at a distal end,
- an acetabular impactor having a hemispherical head at a distal end, an axially disposed second threaded annular portion at a proximal end and at least one channel configured as a drill guide, the second threaded annular portion being screwed into the first threaded annular portion removably affixing the handle to the acetabular impactor,
- the hemispherical head being configured to couple to the acetabular cup, the hemispherical head comprising an annular recess to receive the acetabular cup stem and retaining tabs configured to releasably engage the circumferential groove,
- the method comprising releasably engaging the acetabular cup with the orthopedic instrument,
- positioning the acetabular cup in the acetabular socket,
- impacting the impactor head to set the acetabular cup in the acetabular socket,
- unscrewing the handle from the acetabular impactor,
- drilling a screw hole in the pelvic bone using at least one channel configured as a drill guide,
- passing a screw into the channel and threading the screw into the screw hole, and
- releasing the orthopedic instrument from the acetabular cup.

* * * * *